United States Patent [19]
Kakinuma et al.

[11] B 4,014,860
[45] Mar. 29, 1977

[54] PLASMINOSTREPTIN (ENZYME INHIBITOR) AND METHOD FOR PRODUCING IT FROM STREPTOMYCES

[75] Inventors: Atsushi Kakinuma, Kyoto; Hiromu Sugino, Toyonaka; Norihiko Moriya, Ikeda; Masao Isono, Nishinomiya, all of Japan

[73] Assignee: Takeda Chemical Industries, Ltd., Osaka, Japan

[22] Filed: Jan. 30, 1973

[21] Appl. No.: 328,077

[44] Published under the second Trial Voluntary Protest Program on April 13, 1976 as document No. B 328,077.

[30] Foreign Application Priority Data

Feb. 8, 1972  Japan ............................. 47-14132

[52] U.S. Cl. .......................... 260/112 R; 195/80 R
[51] Int. Cl.$^2$ .................... C12D 13/06; C07G 7/00
[58] Field of Search ........................ 195/65, 80 R; 260/112 R

[56] References Cited
UNITED STATES PATENTS 3,740,319   6/1973   Umezawa et al. ............... 195/80 R

*Primary Examiner*—Lionel M. Shapiro
*Attorney, Agent, or Firm*—Wenderoth, Lind & Ponack

[57] ABSTRACT

Process for producing plasminostreptin by cultivating a Streptomyces microorganism.

4 Claims, 2 Drawing Figures

PLASMINOSTREPTIN (ENZYME INHIBITOR) AND METHOD FOR PRODUCING IT FROM STREPTOMYCES

This invention relates to plasminostreptin, a novel protease inhibitor, and a method for the production thereof.

In an attempt to find new protease inhibitors from the microbial world usable for medical application, the present inventors have conducted extensive studies and examined a number of microorganisms from various soil samples, with the result that several strains of the genus Streptomyces are capable of accumulating a substance which strongly inhibits the activity of plasmin, trypsin and certain alkaline proteases. Subsequent studies enabled the inventors to isolate this substance as crystals. The present inventors named this substance 'plasminostreptin' and after further studies completed a method for producing this substance. Thus, the main object of this invention is to provide the novel protease inhibitor, plasminostreptin.

The other object of this invention is to provide a method for the production of plasminostreptin. These objects are realized by cultivating a microorganism of the genus Streptomyces(e.g. *Streptomyces antifibrinolyticus*), which is capable of accumulating plasminostreptin, in a medium to cause said microorganism to produce plasminostreptin in the resultant culture broth and subsequently recovering plasminostreptin from said broth.

Figure 1:
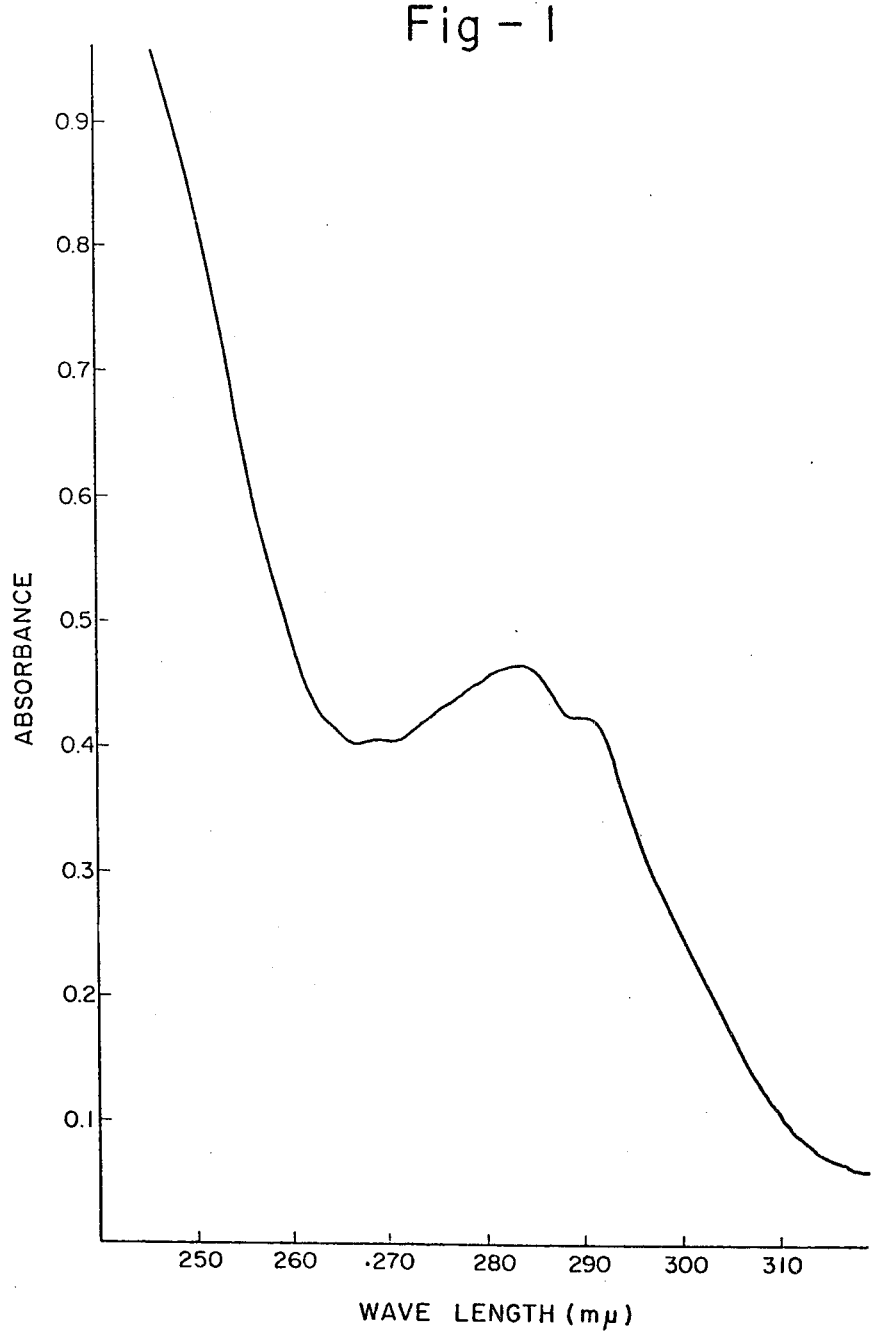
Figure 2:
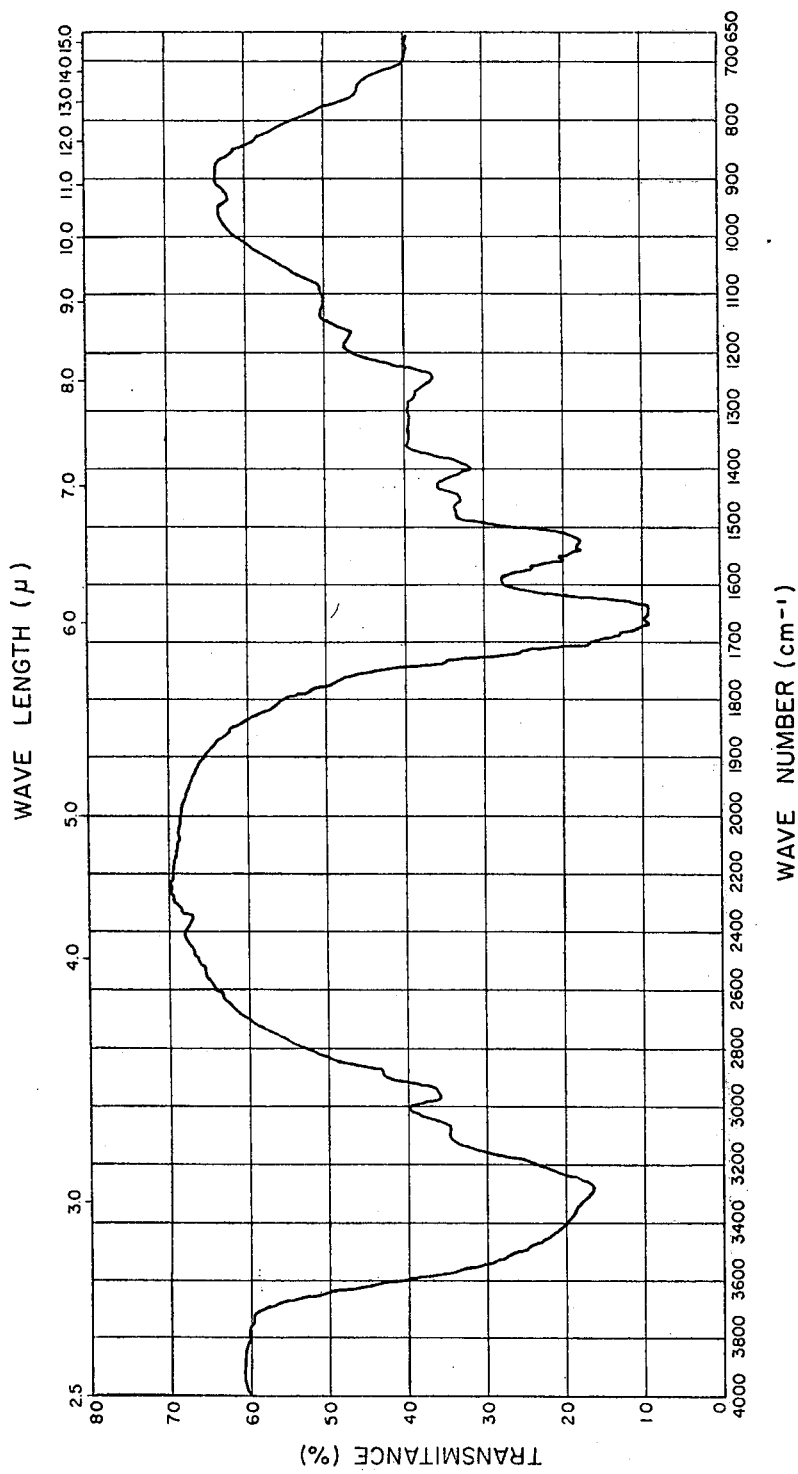

FIG. 1 and FIG. 2 represent the ultraviolet absorption spectrum and infrared absorption spectrum, respectively, of the plasminostreptin obtained according to Example 1 described hereinafter.

The microorganisms to be employed in the working of the present invention are plasminostreptin - producing strains of the genus Streptomyces, more specifically, of *Streptomyces antifibrinolyticus*, and these strains can be screened and isolated with comparative ease from soil samples by the fibrin plate method which will hereinafter be described.

Thus, a candidate Streptomyces organism which has been isolated by means of a per se routine agar medium for the isolation of a strain of the genus Streptomyces is cultivated in a liquid medium and the plasmin-inhibiting activity of the resulting culture is determined on a fibrin plate in which fibrin functions as substrate of plasmin (fibrinolysin).

The plasminostreptin-producing organisms which the inventors have isolated from soil samples by the above method include among others *Streptomyces antifibrinolyticus* No. 10123 (IFO 13298), No. 15807 (IFO 13507), and No. 21211 (IFO 13508). These three strains were isolated from soil samples harvested at Nagaokakyo, Kyoto, Japan; at Nishinomiya, Hyogo, Japan and at Iyomishima, Ehime, Japan, respectively. Cultures of each of these organisms have been deposited at American Type Culture Collection in Rockville, Maryland under accession numbers ATCC 21869, 21870 and 21871, respectively.

The strain No. 10123 has the following microbiological characteristics.

1. Morphological Characteristics:
    Abundant and fluffy aerial mycelium The main stem develops well, and is irregularly branched. Open spiral is formed at the terminal of each conidiophore which bears tens of spores in chain. The spores are spherical to oval and have smooth surfaces.
2. Cultural characteristics:
    1. Glucose - asparagine agar: Aerial mycelium: Grayish white with a cast of brown Substrate mycelium: Yellowish brown to dark brown Soluble pigment: Pale yellowish brown
    2. Glycerin-asparagine agar:
    Aerial mycelium: Grayish white with a scarcely discernible hint of brown
    Substrate mycelium: Yellowish brown with a cast of gray
    Soluble pigment: Very scanty, light yellowish brown
    3. Starch agar: Aerial mycelium: Scanty, grayish white Substrate mycelium: Yellowish brown Soluble pigment: Negligible 4.
    Nutrient agar:
    Aerial mycelium: Negligible
    Substrate mycelium: Pale brown with a cast of gray
    Soluble pigment: Negligible
    5. Yeast-malt agar
    Aerial mycelium: Grayish white with a cast of brown
    Substrate mycelium: Yellowish brown with a cast of gray
    Soluble pigment: Negligible
    6. Oatmeal agar:
    Aerial mycelium: Grayish white with a cast of brown
    Substrate mycelium: Yellowish brown with a cast of gray
    Soluble pigment: Negligible
    7. Glucose-bouillon:
    A ring formation on the tube wall, with sediments
    Soluble pigment: brown
3. Physiological characteristics:
    1. Maximal growth at 25° – 30°C, poor growth at 37°C, substantially no growth at 45°C
    2. Gelatin: liquefied
    3. Starch: hydrolyzed
    4. Melanoid pigments: substantially not produced
4. Utilization of carbon sources:
    L-arabinose, D-glucose, sucrose, inositol, L-rhamnose and
    D-mannitol are utilized for growth; Utilization of D-xylose,
    D-fructose and raffinose is doubtful.

Comparison of the above bacteriological characters with the characters of known Streptomyces species as described in, for example, Bergeys Manual of Determinative Bacteriology, 7th ed. (1957) does not show a microorganism completely identifiable with the present strain whose features are: the conidiophores form openspirals; the aerial mycelium is grayish on synthetic agars; the substrate mycelium is yellowish brown; and soluble pigments are produced.

Thus, the present inventors determined this strain to be of a new species and named it *Streptomyces antifibrinolyticus*.

As the other two strains Nos. 15807 and 21211 share many features with No. 10123 except for some slight differences in colors of aerial and substrate mycelia on yeast-malt agar, they can also be identified as strains of the same new species.

Said three strains are deposited at the Institute for Fermentation (Osaka), Japan, with the accession numbers of 13507, 13508 and 13298, respectively.

In the method of this invention, a plasminostreptin-producing strain of *Streptomyces antifibrinolyticus* is cultivated aerobically in a culture medium.

While the medium may be a solid or a liquid media, it is generally convenient to employ a liquid medium and to grow the microorganism by shake culture or submerged culture. The composition of the medium is optional, the only requisite being that the plasminostreptin-producing strain may grow on it to elaborate and accumulate plasminostreptin.

Thus, one may employ, as carbon sources, such ingredients as glucose, glycerin, starch, sucrose, dextrin, molasses, organic acids, etc.; and as nitrogen sources, such ingredients as protein hydrolysates, e.g. peptone, casamino acids (Difco), N-Z-amine A (Sheffield) etc., meat extract, yeast extract, soybean cake, corn steep liquor, amino acids, ammonium salts, nitrates, and other organic and inorganic nitrogenous compounds.

As inorganic salts, one may incorporate in the medium various phosphates, magnesium sulfate, sodium chloride, etc. In addition, to promote growth of the microorganism, one may add various vitamins, nucleic acid - related compounds and so forth. Depending upon the cultural method and conditions chosen, the addition of an antifoam such as silicone oil, a propylene glycol derivative or soybean oil may be effective for an increased accumulation of plasminostreptin.

In cultivating the microorganism, it is desirable to carry out a small-scale preculture and, thereafter, inoculate the medium with the resulting culture.

Culture conditions including the temperature, time of incubation and the pH of the medium may be selected and controlled so that the accumulation of plasminostreptin will be maximal.

In many instances, it is desirable to carry out an aerated culture at 20° to 37°C for 1 to 6 days, the pH of the medium being maintained at 4.0 to 9.5 throughout the incubation period.

The culture broth obtainable by the cultivation of a plasminostreptin - producing strain contains plasminostreptin. When a liquid medium is employed, a predominant portion of elaborated plasminostreptin accumulates in the liquid phase. Therefore, it is advantageous to remove the mycelia from the broth by filtration or centrifugation and, then, separate plasminostreptin from the residual filtrate or supernatant. This does not mean, however, that one cannot separate plasminostreptin directly from the culture broth, bypassing the mycelium-removal procedure. Separation and purification of plasminostreptin from the culture broth can be easily effected by a suitable combination of per se known techniques, the combination being dependent upon the chemical and physical characteristics of plasminostreptin. Thus, one may for example have resort to such techniques as precipitation with a suitable inorganic salt, e.g. ammonium sulfate; isoelectric precipitation in the neighborhood of the isoelectric point of plasminostreptin, i.e. about pH 6; precipitation with water-miscible organic solvents such as acetone; gel filtration on columns of various types of dextran beads e.g. Sephadex(Pharmacia); ion-exchange chromatography using such ion exchangers as DEAE-cellulose (Midori juji), DEAE-Sephadex (Pharmacia), etc.; adsorption chromatography on various adsorbents such as activated carbon, silica gel, Asmit (Imacti), etc.; dialytic removal of low molecular weight impurities by means of, say, a suitable semipermeable membrane, e.g. a cellophane bag; and the like. Of course one may employ, aside from the above enumerated techniques, any other purification procedures suited for the characteristics of plasminostreptin. By using these techniques in a suitable combination, plasminostreptin can be recovered from the culture broth in an optional purity. The ultimate purified product can be obtained in a crystalline state.

The crystalline preparation of plasminostreptin obtained according to Example 1 which appears hereinafter has the following physicochemical properties.

1. Appearance: White crystals
2. Molecular weight: 26000 ± 2000 as determined in 0.1M sodium chloride by Archibald's ultracentrifugal method [Journal of Physical and Colloid Chemistry, 51, 1204( 1947)]; 25000 ± 2000 as determined in 0.05 M tris (hydroxymethyl) aminomethanehydrochloride buffer (hereafter simply referred to as Tris-HCl buffer) 0.1 M potassium chloride by Andrews' gel filtration method [Biochemical Journal, 91, 222 (1964)] using Sephadex G-75 and Sephadex G-100.

When measured in a certain solvents, however, the molecular weight drops to about half of the above value as shown in Table 1.

Table 1

| Solvent | Means of analysis | Molecular weight |
|---|---|---|
| 4M guanidine hydrochloride — 0.05M Tris-HCl buffer — 0.1M potassium chloride (pH7.5) | Gel filtration on Sephadex G-100 | 11,000 ± 2,000 |
| 0.1% sodium lauryl sulfate | Electrophoresis on polyacrylamide gel | 11,700 ± 2,000 |
| 0.1% sodium lauryl sulfate — 0.05M Tris-HCl buffer (pH7.5) | Gel filtration on Sephadex G-200 | 12,000 ± 2,000 |
| 0.1M formic acid | Gel filtration on Sephadex G-100 | 14,000 ± 2,000 |

3. Sedimentation constant

Sedimentation constant (S 20,w) measured by ultracentrifugation in a synthetic boundary cell is 2.5 ± 0.3 S in 0.1 M sodium chloride and 1.2 ± 0.3 S in 4M guanidine hydrochloride, respectively. The latter sample which gave a sedimentation constant of 1.2 ± 0.3 S was measured again, after being subjected to dialysis at 5°C against one hundred times as much volume of 0.1M sodium chloride, to give a sedimentation constant of 2.5 ± 0.3S.

4. Elemental analysis indicating

C, 51.48 ± 2.0%; H, 6.96 ± 0.5%; N, 16.63 ± 1.0%; S, 1.84 ± 0.5%

5. $[\alpha]_D^{23}$ —90°, approx. (1%,weakly alkaline water)

6. Isoelectric point: about 6.3 as determined by the isoelectric focussing method Acta Chemica Scandinavica,20, 820 (1966).
7. Ultraviolet absorption : its 0.05% solution in 0.1M sodium chloride gives maximum absorption at 283 m$\mu$ minimum absorption at 267 m$\mu$
shoulder at 288 – 291 m$\mu$ (FIG. 1)
8. Infrared absorption (FIG. 2): The significant absorption bands in KBr disc are as follows [wave number (cm$^{-1}$)]:
3280, 3070, 2960, 1670, 1640, 1530, 1400, 1240, 1160
9. Components: When hydrolyzed in 100 parts by volume of 6N-HCl at 105°C for 24 hours, the crystals give the following amino acids: alanine, valine, glycine, threonine, aspartic acid, glutamic acid, leucine, phenylalanine, arginine, proline, serine, cystine (cysteic acid), lysine, tyrosine, histidine and methionine. Isoleucine is not detected. As tryptophan is decomposed under this condition, it was detected by means of ultraviolet absorption [Biochemical Journal 40, 628 (1946)]; while the other amino acids were quantitatively analyzed by an amino acid analyzer. The result is shown as an average of three experiments in Table 2.

Table 2

| Amino Acid | Content (weight %) |
| --- | --- |
| lysine | 3.31 ± 0.20 |
| histidine | 2.37 ± 0.14 |
| arginine | 6.72 ± 0.40 |
| aspartic acid | 10.55 ± 0.76 |
| threonine | 9.57 ± 0.56 |
| serine | 3.75 ± 0.22 |
| glutamic acid | 8.14 ± 1.12 |
| proline | 4.45 ± 0.92 |
| glycine | 5.73 ± 0.36 |
| alanine | 9.78 ± 1.08 |
| half-cystine | 3.53 ± 0.20 |
| valine | 10.52 ± 1.04 |
| methionine | 2.27 ± 0.14 |
| leucine | 7.14 ± 0.98 |
| tyrosine | 4.22 ± 0.24 |
| phenylalanine | 6.34 ± 0.36 |
| tryptophan | 1.61 ± 0.10 |

10. Color reaction:
hypochlorite reagent: positive Folin-Ciocalteu reagent: positive
11. Solubility:
Soluble in water and aqueous ammonia, slightly soluble in pyridine, but only sparingly soluble in glacial acetic acid, alcohols, acetone, chloroform, ether, hexane and other organic solvents. In an aqueous solution, plasminostreptin is almost completely precipitated by ammonium sulfate at 60% saturation and its solubility drops in the neighborhood of pH 6.
12. Stability:
More than 50 percent of the original activity remains intact even after a 30 minutes' treatment at pH 4–9 and at 100°C.
13. Dialytic behavior:
When dissolved in water (pH 8.0) to a concentration of 10 mg/ml, and dialyzed in a cellophane bag against ten times as much volume of water (pH 8.0) at 4°C for 24 hours with stirring, almost all the activity remains in the internal solution.

The physicochemical properties of plasminostreptin crystals are set forth above. Given below is a detailed description of the protease-inhibiting activity of the present substance.

Listed below are the materials and procedures used in the determination of the protease-inhibiting activity of plasminostreptin.
1. Proteases
1. Plasmin-SK: The euglobulin fraction obtained from human blood plasma is dissolved in buffer (1) which is described below and then, activated with streptokinase (Lederle) [Annual Report of Takeda Research Laboratories, 28, 140 (1969)]. 2. Plasmin - UK (Midorijuji, urokinase-activated plasmin) 3. Trypsin (Sigma, crystalline, Type III) 4. Fusarium crystalline alkaline protease (U.S.P. No. 3652399) 5. Nagarse(crystalline protease, Nagase Sangyo) 6. Thrombin (Mochida) 2. Substrates 1. Fibrinogen (Armour, bovine fraction I) 2. Casein (Merck, Hammarsten casein) 3. Buffers 1. 0.02 M Tris-HCl buffer - 0.145 M sodium chloride (pH 7.4) 2. 0.02 M Tris-HCl buffer (pH 7.4) 3. 0.1 M glycine - NaOH buffer (pH 10.5)
4. Methods for analysis
1. Plasmin-fibrin system (fibrin plate method): Ten ml of a fibrinogen solution (1%, buffer (1) is placed in a petri dish (9 cm in diameter) and gelled by the addition of 0.2 ml of thrombin [50 J. P. units (Japanese Pharmacopeia units)/ml, 0.145 M sodium chloride]. The gel is allowed to stand at 30°C for 30 minutes to prepare a fibrin plate. Meanwhile, paper discs (8mm in diameter, water-absorbing capacity: 0.025 ml) are dipped in a plasminostreptin solution of varying concentrations and allowed to dry on a filter paper in the air.
Then, 0.015 ml of a plasmin-SK solution is dropped onto each of the discs, which is placed on the above fibrin plate. After the system is allowed to stand at 37°C for 5 to 10 hours, the formation of lyzed zone in evaluated. The plasmin-inhibiting activity of plasminostreptin is indicated as the concentration of plasminostreptin solution required for a complete inhibition of fibrinolysis. (2) Plasmin-fibrin system (determination of clot lysis time): Into a small test tube are poured 0.4 ml of a fibrinogen solution (0.25%, buffer (1)), 0.3 ml of buffer (1) and 0.1 ml of plasminostreptin solution of varying concentrations, followed by the addition of 0.1 ml of a plasmin-UK solution 0.8 casein units/ml, buffer (1). The mixture in blended well and immediately thereafter, 0.1 ml of a thrombin solution (50 J. P. units/ml, 0.145 M sodium chloride) is added. The resulting gel is allowed to stand at 37°C and the time necessary to lyse the clot is measured. The plasmin-inhibiting activity of plasminostreptin is determined by the procedure set forth in Biochimica Biophysica Acta. 214, 411 (1970). Thus, the amount of plasminostreptin which is required for a 50% inhibition of the activity of 0.08 casein units of plasmin-UK, which occurs in the reaction mixture, is determined from the concentration of plasminostreptin which will double the clot lysis time in the absence of plasminostreptin, and the above amount is indicated in units of ID$_{50}$. 3. Plasmin-casein system: Into a test tube are poured 1 ml of casein solution [4%, buffer (2)], 0.5 ml of buffer (2) and 0.3 ml of a plasminostreptin solution of varying concentrations, followed by the addition of 0.2 ml of plasminUK solution [2 casein units/ml, buffer (2)]. The mixture is blended well and allowed to stand at 37°C for 20 minutes. The reaction is terminated by the addition of 2 ml of 1.7 M perchloric acid and the system is allowed to stand at room temperature for another 1 hour. The reaction mixture is filtered through a filter paper and the absorbance of the resulting filtrate at 280 m$\mu$ is measured.

The plasmin-inhibiting activity of plasminostreptin is determined and indicated as follows.

Thus, the amount of plasminostreptin is determined which is required to effect a 50% inhibition of the activity of 0.4 casein units of plasmin-UK in the absence of plasminostreptin and is shown in units of $ID_{50}$.

4. Trypsin-casein system:

Into a test tube are poured 1 ml of a casein solution [2%, buffer (2)], 0.5 ml of buffer (2) and 0.3 ml of a plasminostreptin solution of varying concentrations and after the addition of 0.2 ml of a trypsin solution [50 $\mu$g/ml, buffer(2)], the mixture is blended well and allowed to stand under conditions similar to those described for the plasmin-casein system. Thereafter, also in the same manner as described above, the amount of plasminostreptin required for a 50% inhibition of the activity of 10 $\mu$g of trypsin in the absence of plasminostreptin is determined and indicated in units of $ID_{50}$.

5. Fusarium alkaline protease - casein system and Nagarse - casein system:

Into a test tube are poured 1 ml of a casein solution [2%, buffer (3)], 0.5 ml of buffer (3), and 0.4 ml of a plasminostreptin solution of varying concentration and after the addition of 0.1 ml of either a Fusarium alkaline protease solution [40 $\mu$g/ml, buffer (3)] or Nagarse solution [100 $\mu$g/ml, buffer (3)], the mixture is blended well and allowed to stand under conditions similar to those described for the plasmin-casein system. Thereafter, also in the same manner as described above, the amount of plasminostreptin required for a 50% inhibition of the activity of 4 $\mu$g of Fusarium alkaline protease and 10 $\mu$g of Nagarse in the absence of plasminostreptin is determined, respectively, and indicated in units of $ID_{50}$.

The activities of plasminostreptin to inhibit plasmin, trypsin and alkaline proteases, as measured in the foregoing manners are shown in Table 3.

Table 3

| Protease-substrate | Protease-inhibiting activity | |
|---|---|---|
| | Concentration for complete inhibition ($\mu$g/ml) | $ID_{50}$ ($\mu$g) |
| Plasmin-fibrin (fibrin plate) | <30 | |
| Plasmin-fibrin (clot lysis time) | | <10 |
| Plasmin-casein | | <10 |
| Trypsin-casein | | <5 |
| Fusasium alkaline protease-casein | | <6 |
| Nagarse-casein | | <5 |

Inhibition of the activity of kallikrein (Beyer, Depot - Padutin) by plasminostreptin can hardly be detected. By way of example, 50% inhibition of the esterase activity of 0.8 biological unit of said kallikrein against benzoylarginine ethyl ester was not made by less than 800 $\mu$g of plasminostreptin.

From each of five rats (male, SD, 7 weeks old), blood samples are taken before the administration of plasminostreptin and also 1 hour after the intravenous administration of 0.8 mg plasminostreptin. The plasma is separated from each of the blood samples and the abovementioned plasmin-UK solution is added in each plasma sample to various concentrations.

Immediately thereafter, the activity of plasmin in each plasma sample is determined using casein as substrate. The plasmin activity of blood plasma samples from each rat before and after the administration of plasminostreptin are compared. The result shows that the plasmin activity is significantly inhibited by the administration of plasminostreptin. The degree of inhibition of plasmin activity as measured after the addition of 100 casein units of plasmin-UK to each 1 ml. of plasma are 3 to 35% (18% on the average).

The toxicity of plasminostreptin is extremely low and its $LD_{50}$ values as determined by acute toxicity tests in mice are more than 5 g/kg orally, more than 5 g/kg intraperitoneally and 2 to 3 g/kg, intravenously.

Plasminostreptin is characterized by its prominent propensity to inhibit the proteolytic activity of plasmin and of trypsin and it is of wide use in medical applications, i.e. as prophylactic and therapeutic agents for various pancreatic disorders, inflammations, external injuries and hemorrhage based on fibrinolysinemia which may be especially encountered, for instance, at obstetric, urinological or surgical operations.

Although the dosing route and dosage in medical applications vary with the kinds of diseases, degree of symptoms, etc., plasminostreptin is usually applied topically, or by injection or dropping into veins. In the case of intraveneous dropping about 5 mg to about 5 g of dose per day may be given to a human adult for several days.

Described above are the process for the production, the physicochemical properties, the protease-inhibiting activities and the applications of plasminostreptin, a novel protease inhibitor which has been successfully isolated from the cultures of strains of the genus Streptomyces, more specifically, of *Streptomyces antifibrinolyticus*, and purified in crystalline form by the present inventors. Now, the process for the production of this inhibitor according to this invention will be further described in the following examples.

In the following examples, 'parts by weight' bears the same relation to 'parts by volume' as does 'gram(s)' to 'milliliter(s)' and percent is calculated on weight by volume basis.

EXAMPLE 1

*Streptomyces antifibrinolyticus* No. 10123 (IFO 13298), which has been grown at 28°C for 7 days on an agar medium (pH 7.3) containing 1% glucose, 0.1% yeast extract, 0.1% meat extract, 0.2% N-Z-amine A (Sheffield) and 2% agar, is used to inoculate 40 parts by volume of a liquid medium (pH 7.0) composed of 1% glucose, 1% peptone, 0.7% meat extract, 0.3% sodium chloride and 0.2% potassium monohydrogen phosphate placed in a flask of 200 parts by volume in capacity. The system is incubated on a rotary shaker at 28°C for 2 days and the resulting culture is transferred to fermentor of 2000 parts by volume in capacity containing 500 parts by volume of the same liquid medium as above.

The system is incubated under aeration and stirring at 28°C for 2 days, whereupon 500 parts by volume of a culture broth is obtained. The broth is used to inoculate 30,000 parts by volume of the same liquid medium as above contained in a fermentor of 50,000 parts by volume in capacity and, with the addition of 50 parts by weight of an antifoaming agent, a submerged culture is carried out at 28°C for 48 hours.

After the cultivation has been completed, the broth is filtered on a filter press using diatomaceus earth as a filter aid, whereupon 28,000 parts by volume of a filtrate is obtained. Crystals of ammonium sulfate are added to the above filtrate to 60% saturation and the system is stirred at room temperature for about 3 hours. The precipitates are recovered by filtration through a filter press using Hyflo Super Cel again. The cake includes Hyflo Super Cel. Therefore, after the addition of weakly alkaline water, the cake is stirred in a container and filtered. The filtrate is taken and the cake is washed with water. The above procedure is repeated and the filtrates are pooled (10,000 parts by volume) and concentrated under reduced pressure at 50°C to 2,000 parts by volume. The concentrate is dialyzed against running water using a cellophane bag for 2 days. After the ammonium sulfate has been removed, the residue is adsorbed on a column of DEAE-cellulose, which has been previously treated with 0.5N hydrochloric acid and 0.5N sodium hydroxide and, then, thoroughly washed with water. The column is washed well with water and, then, the active substance is eluted with 0.05M sodium chloride. The active fractions are pooled and lyophilized, whereupon a powder which is white with a cast of yellow is obtained. This powder is dissolved in distilled water and the solution is passed through a column of Sephadex G-15.

The active fractions are pooled, concentrated and allowed to stand, whereupon white crystals separate out. The crystals are recovered by filtration and the mother fluid is concentrated to recover further ammounts of crystals. The crystals are combined and dissolved in weakly alkaline water to a concentration of 3–5%.

The solution is brought to pH about 6 and, then, allowed to stand at room temperature, whereupon white crystals appear again.

These crystals are recovered by filtration and washed several times with distilled water at pH 6, followed by drying. The procedure yields 1.8 parts by weight of crystalline plasminostreptin. The above crystalline product gives a single band in disc electrophresis on polyacrylamide gel, and shows a single peak in ultra-centrifugal analysis. Further, the concentration of this product for a complete inhibition of fibrinolysis as determined by the fibrin plate method described in this specification is 20 μg./ml.

EXAMPLE 2

*Streptomyces antifibrinolyticus* No. 15807 (IFO 13507), which has been grown at 28°C for 5 days on an agar medium (pH 7.3) containing 1% maltose, 0.1% yeast extract, 0.1% meat extract, 0.2% N-Z-amin A (Sheffield) and 2% agar, is used to inoculate 40 parts by volume of a liquid medium (pH 7.0) composed of 1% glucose, 1% peptone, 0.7% meat extract, 0.3% sodium chloride and 0.2% potassium monohydrogen phosphate contained in a flask of 200 parts by volume in capacity. The system is incubated on a rotary shaker at 28°C for 3 days and the resulting culture is transferred to a fermentor of 2000 parts by volume in capacity containing 500 parts by volume of the same liquid medium as above.

The fermentor is incubated under aeration and stirring at 28°C for 3 days, whereupon 500 parts by volume of a culture broth is obtained. The broth is used to inoculate a fermentor of 50,000 parts by volume in capacity containing 30,000 parts by volume of the same liquid medium as above and, with the addition of 50 parts by weight of an antifoaming agent, a submerged culture is carried out at 28°C for 60 hrs. This culture broth is transferred to a fermentor of 2,000,000 parts by volume in capacity containing 1,000,000 parts by volume of the same liquid medium and, with the addition of 500 parts by weight of said antifoam agent, further cultivation is continued at 28°C for 60 hours under aeration and stirring.

After cultivation has been completed, the broth is filtered by means of a filter press using diatomaceus earth as a filter aid, whereupon 980,000 parts by volume of a filtrate is obtained. Crystals of ammonium sulfate are added to the above filtrate to 60% saturation and the system is stirred at room temperature for about 3 hours. The precipitates are recovered again by filtration through a filter press using Hyflo Super Cel. To the cake is added 50,000 parts by volume of water under stirring and the mixture is filtered. This procedure is repeated and the filtrate is pooled (100,000 parts by volume).

Crystals of ammonium sulfate are added to the combined filtrate to 60% saturation. The system is filtered and the cake is washed twice with 15,000 parts by volume of water each and filtered. The filtrates are combined and chromatographed on a column of DEA-Ecellulose of 3,000 parts by volume, which has been previously treated with 0.5n hydrochloric acid and 0.5N sodium hydroxide and, then, thoroughly washed with water, and the column is washed with 10,000 parts by volume of water.

To 40,000 parts by volume of the combined solution of eluate and washings are added crystals of ammonium sulfate to 50% saturation and the mixture is filtered on a Buchner filter to collect pricipitates. The precipitates are dissolved in 7,000 parts by volume of 0.05 M Tris-HCl buffer (pH 7.5) and the undissolved substances are filtered off. The filtrate is passed for desalting through a column of Sephadex G-15 (above mentioned), which has been previously washed with the same buffer as above, and the active fractions are pooled and passed through a column of DEAE-cellulose (1,500 parts by volume), which has been previously treated with the same buffer as above, to give 25,000 parts by volume of the eluate. To the eluate are added crystals of ammonium sulfate to 50% saturation, and the resulting precipitates are collected by centrifugation and dissolved in 4,000 parts by volume of distilled water. The solution is passed for desalting through a column of Sephadex G-15. The resulting 6,000 parts by volume of the active fractions are allowed to stand at 5°C to give 45 parts by weight of white crystals (dry basis), which coincide with the preparation of plasminostreptin obtained in Example 1 in physicochemical properties and the protease-inhibiting activity.

EXAMPLE 3

In a manner similar to example 2, Streptomyces antifibrinolyticus No. 21211 (IFO 13508) is cultivated and the resulting 950,000 parts by volume of the culture broth is subjected to the purification procedure mentioned in Example 2 but using 5,000 parts by volume of Asmit 173 N (Imacti) column instead of 3,000 parts by volume of DEAE-cellulose column in Example 2.

The yield is 30 parts by weight of white crystals of plasminostreptin.

What we claim is:

1. Plasminostreptin, capable of inhibiting the proteolytic activity of plasmin and trypsin, characterized by the following properties:

a. a molecular weight of 26,000 ± 2,000 as determined in 0.1 M sodium chloride by Archibald's ultracentrifugal method, and 25,000 ± 2,000 as determined in 0.05 M Tris-HCl buffer-0.1 M potassium chloride by Andrews' gel filtration method,
b. sedimentation constant ($S_{20}$, w), by ultracentrifugation, of 2.5 ± 0.3 S in 0.1 M sodium chloride and 1.2 ± 0.3 S in 4 M guanidine hydrochloride,
c. elemental analysis indicating C, 51.48 ± 2.0%; H, 6.96 ± 0.5%; N, 16.63 ± 1.0%; and S, 1.84 ± 0.5%,
d. specific rotation $[\alpha]_D^{23}$ of about −90° (C=1, in a weakly alkaline solution),
e. isoelectric point of about 6.3 as determined by the isoelectric focussing method,
f. 0.05% solution thereof in 0.1 M sodium chloride gives a maximum absorption at 283 mμ, a minimum absorption at 267 mμ and a shoulder at 288 to 291 mμ,
g. significant infrared absorption bands at wave numbers ($cm^{-1}$) 3280, 3070, 2960, 1670, 1640, 1530, 1400, 1240 and 1160.
h. contains alanine, valine, glycine, threonine, aspartic acid, glutamic acid, leucine, phenylalanine, arginine, proline, serine, cystine or cysteine, lysine, tyrosine, histidine, methionine and tryptophan, and does not contain isoleucine,
i. positive to hypochlorite reagent and Folin-Ciocalteu reagent,
j. soluble in water and aqueous ammonia; slightly soluble in pyridine; sparingly soluble in glacial acetic acid, alcohols, acetone, chloroform, ether and hexane; substantially completely precipitated by ammonium sulfate at 60% saturation and solubility dropping in the neighborhood of pH 6,
k. more than 50% of the initial activity thereof remains intact after treatment for 30 minutes at pH 4–9 and 100°C, and
l. dialytic behavior indicating substantially all the activity thereof remains in the internal solution, when dissolved in water having a pH of 8.0 to a concentration of 10 mg./ml and dialyzed in a cellophane bag against ten times as much volume of water having a pH of 8.0 to 4°C for 24 hours.

2. A process for producing plasminostreptin as defined in claim 1, which comprises cultivating a plasminostreptin-producing microorganism of the genus Streptomyces in a culture medium containing an assimilable carbon source and a digestible nitrogen source under aerobic conditions until plasminostreptin is accumulated in the culture broth, and recovering the accumulated plasminostreptin from the culture broth.

3. The process according to claim 2, wherein the microorganism is *Streptomyces antifibrinolyticus*.

4. The process according to claim 3, wherein the microorganism is *Streptomyces antifibrinolyticus* ATCC 21869, ATCC 21870 or ATCC 21871.

* * * * *